(12) United States Patent
Meyer

(10) Patent No.: US 8,052,971 B2
(45) Date of Patent: Nov. 8, 2011

(54) ORAL USE OF SPECIFIC ANTIBODIES FOR INTESTINAL HEALTH

(75) Inventor: Mark Meyer, Ames, IA (US)

(73) Assignee: MG Biologics, Ames, IA (US)

( * ) Notice: Subject to any disclaimer, the term of this patent is extended or adjusted under 35 U.S.C. 154(b) by 0 days.

(21) Appl. No.: 11/602,160

(22) Filed: Nov. 20, 2006

(65) Prior Publication Data

US 2007/0154484 A1     Jul. 5, 2007

Related U.S. Application Data

(60) Provisional application No. 60/738,633, filed on Nov. 21, 2005.

(51) Int. Cl.
    *A61K 39/395*     (2006.01)
    *A61K 39/42*     (2006.01)
    *A61K 39/00*     (2006.01)

(52) U.S. Cl. .............. 424/130.1; 424/145.1; 424/147.1; 424/184.1

(58) Field of Classification Search .................. None
See application file for complete search history.

(56) References Cited

U.S. PATENT DOCUMENTS

| | | | |
|---|---|---|---|
| 4,925,920 A | 5/1990 | Mannick et al. |
| 5,039,521 A | 8/1991 | Bolton et al. |
| 5,109,118 A | 4/1992 | Mizushima |
| 5,122,368 A | 6/1992 | Greenfield et al. |
| 5,171,578 A | 12/1992 | Bally et al. |
| 5,308,835 A | 5/1994 | Clements |
| 5,316,764 A | 5/1994 | Walsh |
| 5,885,585 A | 3/1999 | Parrish et al. |
| 6,048,527 A | 4/2000 | Granoff et al. |
| 6,193,966 B1 | 2/2001 | Deo et al. |
| 6,214,343 B1 | 4/2001 | Kink et al. |
| 6,241,992 B1 | 6/2001 | Morck et al. |
| 6,333,032 B1 | 12/2001 | Skurkovich et al. |
| 6,503,511 B1 | 1/2003 | Wizemann et al. |
| 6,610,306 B2 | 8/2003 | Judd et al. |
| 6,746,673 B2 | 6/2004 | Serizawa et al. |
| 6,793,921 B2 | 9/2004 | Kodama et al. |
| 6,833,356 B1 | 12/2004 | Koenig et al. |
| 6,863,893 B2 | 3/2005 | Wizemann et al. |
| 6,866,849 B2 | 3/2005 | Schenk |
| 6,866,850 B2 | 3/2005 | Schenk |
| 6,887,480 B1 | 5/2005 | Adamou et al. |
| 6,905,686 B1 | 6/2005 | Schenk |
| 2001/0026798 A1 | 10/2001 | Koenig |
| 2001/0029251 A1 | 10/2001 | Gonczol et al. |
| 2002/0025325 A1 | 2/2002 | Chu et al. |
| 2002/0052311 A1 | 5/2002 | Solomon et al. |
| 2003/0092145 A1 | 5/2003 | Jira et al. |
| 2003/0118596 A1 | 6/2003 | Pogue et al. |
| 2003/0138456 A1 | 7/2003 | Arntzen et al. |
| 2005/0106163 A1 | 5/2005 | David et al. |
| 2005/0112130 A1 | 5/2005 | Bhat et al. |

OTHER PUBLICATIONS

Keller et al (Clinical Microbiology Reviews, Oct. 2000, p. 602-614).*
Kaverina et al (SU 1498500 A1 published Aug. 8, 1989)(Abstract only).*
Tackett et al (The New England Journal of Medicine, May 12, 1988, pp. 1240-1243).*
Dougan et al (British Medical Bulletin, 2002:62:113-123).*
Campagnari et al (Microbial Pathogenesis, 1990:8:353-363).*
Shi et al (Pro. Natl. Acad. Sci. USA, Feb. 16, 1999; 964, 1615-20).*
Bartlett et al (AIDS 1998, 12:1291-1300).*

* cited by examiner

*Primary Examiner* — Vanessa L. Ford
(74) *Attorney, Agent, or Firm* — Emily E. Harris; Kent A. Herink

(57) ABSTRACT

Methods and compositions are provided to treat enteric disease. The methods and compositions use passive immunity to treat diseases of the gut, including diseases caused by *Salmonella* sp., *E. Coli*, *Clostridium difficile*, *Clostridium perfringens* A, *Clostridium perfringens* C, *Clostridium perfringens* D, canine distemper, feline distemper, Rotavirus, and Parvovirus. Specific antibodies are administered orally to a subject to improve intestinal health.

6 Claims, No Drawings

ORAL USE OF SPECIFIC ANTIBODIES FOR INTESTINAL HEALTH

This application claims priority to U.S. Patent Application Ser. No. 60/738,633, filed Nov. 21, 2005.

BACKGROUND OF THE INVENTION

The invention relates generally to a treatment for diseases of the gut, and, more particularly, to the oral administration of specific antibodies for treatment of enteric disease.

Enteric diseases include bacterial and viral infections of the gastrointestinal tract, such as *Salmonella, E. Coli, Clostridium difficile, Clostridium perfringens* A, *Clostridium perfringens* C, *Clostridium perfringens* D, canine distemper, feline distemper, Rotavirus, and Parvovirus. These diseases can result in diarrhea and vomiting, which may in turn lead to loss of fluid, anorexia, and malabsorption of nutrients. Humans; livestock, such as cattle, horses, and swine; canines; and felines are all affected by enteric disease.

Traditional methods of treating enteric disease involve active immunization through vaccines or treatment of disease with antibiotics that are grown in a fermenter in a factory. In addition, enteric diseases have also been treated via the systemic administration of fluids and plasma, generally via intravenous administration.

For example, traditional treatments for Parvovirus, a viral disease that primarily affects canines, have included the systemic, intravenous administration of plasma immunized against *E. Coli* gram-negative bacteria. Drawbacks of this method include the frequent occurrence of anaphylactic reaction. In addition, such systemic administration of the plasma generally does not improve health for two to three days. Finally, the traditional method of treating Parvovirus requires a veterinarian to set a catheter and the treatment must be administered by the veterinarian.

It has long been understood that antibodies recognize and neutralize antigens such as bacteria and viruses. Antibodies are generally thought to be degraded in the gut where stomach acids and enzymes break down the proteins for nutrition. Research has shown, though, that antibodies do, in fact, survive the digestive tract. For example, it has been determined that almost half of bovine IgG in an oral dose of bovine immunoglobulin concentrate-*Clostridium difficile* can be retrieved intact from the distal small intestine in humans, and the surviving IgG retains its specific antigen binding activity. (Warny et al, *Bovine Immunogloulin concentrate-Clostridium difficile retains C difficile toxin neutralizing activity after passage through the human stomach and small intestine*. Gut 1999; 44:212-217 (February)). Thus, specific antibodies may be used for the treatment of specific enteric diseases, as well as many kinds of local infections which could be treated with topical treatment with antibodies.

SUMMARY OF THE INVENTION

An object of the invention is to provide a method for treating enteric disease in humans and other mammals.

A further object of the invention is to provide an oral treatment of enteric disease.

Another object of the invention is to provide a method of treating enteric disease by orally administering specific antibodies.

These and other objects of the present invention will become apparent to those skilled in the art upon reference to the following specification, drawings, and claims.

DETAILED DESCRIPTION OF THE INVENTION

The invention comprises a method of treating enteric disease in mammals. In general, the invention comprises administering antibodies orally to a subject. Enteric diseases that may be treated through oral administration of antibodies include enteric diseases caused by *Salmonella* sp., *E. Coli, Clostridium difficile, Clostridium perfringens* A, *Clostridium perfringens* C, *Clostridium perfringens* D, canine distemper, feline distemper, Rotavirus, and Parvovirus. Antibodies may be administered to all species of mammals, including humans, canines, porcines, felines, bovines, and equines.

This invention uses passive immunity to treat enteric disease. Antibodies to a specific antigen are raised in one organism. The antibodies are removed from the host organism and transferred to a recipient. When the antibodies are administered orally, they remain viable and functional in the intestinal tract. These active, functional antibodies attack and neutralize the antigen which has been destroying the villi of the gut and therefore begin improvement of the gut health immediately after administration. The mechanism of action is simply surface contact of the antibody against the antigen.

In one embodiment of this invention, large herd animals, such as horses, cattle, or swine are hyperimmunized for various diseases of the gut, including *Salmonella* sp., *E. Coli, Clostridium difficile, Clostridium perfringens* A, *Clostridium perfringens* C, *Clostridium perfringens* D, canine distemper, feline distemper, Rotavirus, and Parvovirus. Plasma from the hyperimmunized host animal is separated from the host animal's blood using plasmapheresis. The plasma is then administered to a subject orally. The subject can be any species affected by enteric disease. The plasma can be given to the recipient in any of the known methods of oral administration, including tablets, capsules, powders, granules, suspensions, or solutions.

EXAMPLE 1

In this example, the invention acts to provide enteric health to dogs before and after the onset of Parvovirus symptoms. In this instance, a horse is used as the host animal. The horse is vaccinated with a Parvovirus antigen. The immunized horse will demonstrate an immune response and produce antibodies specific to canine Parvovirus. These antibodies are harvested by plasmapheresis collection of the plasma. The plasma that is collected may be administered to a dog orally. In this example, 2 ml/lb body weight is administered one time, with a second administration of the same amount possibly occurring if the animal regurgitates the original dose.

Symptoms of Parvovirus such as vomiting and diarrhea have been observed to be greatly reduced within two hours and eight hours respectively. Within twenty-four hours to forty-eight hours of administration, animals have been observed to be acting normally. Table 1 summarizes reports of veterinarians who have administered one dose of the plasma of this invention to dogs with Parvovirus, or with symptoms of Parvovirus.

TABLE 1

Veterinarian testimony regarding the efficacy of administration of one dose of 2 ml/lb body weight plasma

| Number of Dogs[1] Treated for Parvovirus per Veterinarian | Supplemental Treatments (other than with plasma) | General Condition and Symptoms after Administration of Plasma |
|---|---|---|
| 2 | n/a | |
| 1 | | Vomiting and bloody stools stopped, puppy doing wonderfully |

TABLE 1-continued

Veterinarian testimony regarding the efficacy of administration of one dose of 2 ml/lb body weight plasma

| Number of Dogs[1] Treated for Parvovirus per Veterinarian | Supplemental Treatments (other than with plasma) | General Condition and Symptoms after Administration of Plasma |
|---|---|---|
| 1 | Fluids and antibiotics | Puppy went home |
| 1 | | Good results |
| 1 | | Recovered in 2.5 days and went home |
| 2 | Batril and antibiotic | After 8 hours, vet was amazed at how quickly the pups are feeling better, perking up, less diarrhea |
| 1 | Antibiotic | Pup was sent home immediately after 1 dose, owner indicated puppy recovering very well |
| 1 | Endoserum, Immunoboost | Vet noticed less severity in symptoms |
| 1 | | Pup came in during morning with eyes matted almost shut, could hardly lift head; 4 hours after administration of plasma, pup up wagging tail and ate his food right up, by 8 am next day, he was jumping in pen |
| 4 | | One dose given, 2 pups were better in 2 days, 1 in 4 days, and 1 in 3 days. The vet said the pups were getting better so quickly they kept thinking "can this be true?" |
| 1 | | Pup brought in Monday-very sick and was already up and around Tuesday after treatment with plasma |
| 2 | | 1 pup died<br>1 pup-was stray and very sick & thin, but doing ok after administration of plasma |
| 1 | | Prior to treatment, pup was vomiting and couldn't keep much down; after treatment did recover |
| 3 | | 2 pups doing better, 1 not quite as well, but he was more sick at the start |
| 1 | | Pup had diarrhea and vomiting; 24 hours after dose of plasma, pup doing better |
| 6 | | 5/6 died, but pups were very sick before treatment |
| 1 | fluids | Pup came into vet and he didn't think he would make it-gave one dose of plasma, pup was better in 3-4 days |
| 1 | | Pup brought in on Tuesday, vet tried everything and was ready to give up. Friday administered plasma (1 dose) at 11 am and by noon pup was up barking and eating |
| Not indicated | Vet's standard treatment | The vet hasn't lost anyone. He feels the plasma is helping, but they "throw everything" at a parvo pup-feels plasma has its place |
| 1 | | Pup died |
| 1 | | Three hours after treatment, pup threw up, but after 36 hours has started nibbling and at 48 hours is bouncing off the walls |
| 1 | | Pup is doing great |
| 3 | | All three pups discharged and doing well |
| 5 | | Good results |
| 1 | | Pup went home the day after treatment |
| 1 | Fluids | Very sick dog. After 1 dose he was better in 24 hours |
| 2 | Antibiotics, vitamins, injections | Initial symptoms included general depression, vomiting, watery diarrhea. General condition and symptoms 24 hours after administration: no vomiting. After 48 hours, eating, acting normal. |
| 1 | | After 24 hours, alert, not drinking, no vomiting. After 48 hours, drank and ate, sent home |
| 1 | | After 24 hours, alert, barking, drank some and vomited small amount. After 48 hours, ate and drank, sent home |
| 1 | | A lot better 6 days later. |

[1]One vet treated two kittens with panleukopenia with plasma and they appear healthy Advantages to this invention include the quick time to recovery and the ease with which it is administered.

Effective doses range from 0.5 ml plasma/lb body weight to 10 ml/lb body weight, or more, depending on the subject's capacity for consuming the plasma.

The plasma may be administered alone, or with known treatments. For example, the plasma may be administered to a Parvovirus-infected dog alone, or in conjunction with known treatments such as antibiotics, vitamins, fluids, or intravenous serum.

The foregoing description and drawings comprise illustrative embodiments of the present inventions. The foregoing embodiments and the methods described herein may vary based on the ability, experience, and preference of those skilled in the art. Merely listing the steps of the method in a certain order does not constitute any limitation on the order of the steps of the method. The foregoing description and drawings merely explain and illustrate the invention, and the invention is not limited thereto, except insofar as the claims are so limited. Those skilled in the art who have the disclosure before them will be able to make modifications and variations therein without departing from the scope of the invention.

The invention claimed is:

1. A method of treating enteric disease in a mammal comprising:
   (a) immunizing a first mammal with an enteric antigen;
   (b) harvesting antibodies to the antigen from the first mammal by separating plasma from the mammal's blood; and
   (c) orally administering an effective amount of the antibody-containing plasma to a second mammal in need thereof, wherein the second mammal is a different species than the first mammal.

2. A method as defined in claim 1, wherein the enteric disease is selected from the group consisting enteric diseases caused by *Salmonella* sp., *Escherichia coli*, *Clostridium difficile*, *Clostridium perfringens* A, *Clostridium perfringens* C, *Clostridium perfringens* D, canine distemper, feline distemper, and Rotavirus.

3. A method as defined in claim 1, wherein the first mammal is selected from the group consisting of humans, canines, porcines, felines, bovines, and equines.

4. A method as defined in claim 1, wherein the amount is between 0.5 ml plasma/lb body weight to 10 ml plasma/lb body weight.

5. A method as defined in claim 1, wherein the antigen is Parvovirus.

6. A method as defined in claim 1, wherein the second mammal is selected from the group consisting of humans, canines, porcines, felines, bovines, and equines.

\* \* \* \* \*